United States Patent
Akashi et al.

(10) Patent No.: US 8,263,405 B2
(45) Date of Patent: Sep. 11, 2012

(54) CONTROLLABLY DEGRADABLE HYDROGEL FOR CULTURING CELLS TO PRODUCE THREE-DIMENSIONALLY ORGANIZED CELLS

(75) Inventors: Mitsuru Akashi, Suita (JP); Yoshiki Sawa, Suita (JP); Michiya Matsusaki, Suita (JP)

(73) Assignees: Mitsuru Akashi, Osaka (JP); NOF Corporation, Tokyo (JP)

( * ) Notice: Subject to any disclaimer, the term of this patent is extended or adjusted under 35 U.S.C. 154(b) by 920 days.

(21) Appl. No.: 12/094,973

(22) PCT Filed: Nov. 24, 2006

(86) PCT No.: PCT/JP2006/323458
§ 371 (c)(1),
(2), (4) Date: Jan. 6, 2009

(87) PCT Pub. No.: WO2007/061058
PCT Pub. Date: May 31, 2007

(65) Prior Publication Data
US 2009/0117656 A1    May 7, 2009

(30) Foreign Application Priority Data
Nov. 24, 2005 (JP) .................. 2005-338846

(51) Int. Cl.
*C12N 5/07* (2010.01)
*C12N 11/08* (2006.01)
(52) U.S. Cl. ........................ 435/397; 435/180
(58) Field of Classification Search .......... None
See application file for complete search history.

(56) References Cited

U.S. PATENT DOCUMENTS

| | | | |
|---|---|---|---|
| 5,412,076 A * | 5/1995 | Gagnieu ............... | 530/356 |
| 5,461,085 A | 10/1995 | Nagatomo et al. | |
| 6,579,596 B1 * | 6/2003 | Akashi et al. ....... | 428/195.1 |
| 6,916,909 B1 * | 7/2005 | Nicolas et al. ...... | 530/356 |
| 7,030,208 B2 * | 4/2006 | Yalpani ............... | 528/328 |
| 7,332,527 B2 * | 2/2008 | Bronich et al. ...... | 514/772.1 |
| 7,354,764 B2 * | 4/2008 | Bader .................. | 435/395 |
| 7,790,417 B2 * | 9/2010 | Ho et al. ............. | 435/72 |

FOREIGN PATENT DOCUMENTS

| | | |
|---|---|---|
| JP | 48-80640 A | 10/1973 |
| JP | 7-224163 A | 8/1995 |
| JP | 9-107730 A | 4/1997 |
| JP | 9-503490 A | 4/1997 |
| JP | 2002-504412 A | 2/2002 |
| JP | 2004-533500 A | 11/2004 |
| WO | WO-95/03272 A1 | 2/1995 |
| WO | WO-99/43787 A2 | 9/1999 |
| WO | WO-02/081662 A1 | 10/2002 |

OTHER PUBLICATIONS

Y. Tsuda et al., J. Biomed. Mater. Res 69A, 70-78(2004).
Y. Tsuda et al., Biomaterials 26, 1885-93 (2005).
A. Maya et al., Biomaterials 23, 1121-1130 (2002).
W. Tan. et al., Biomaterials 25, 1355 (2004).

* cited by examiner

*Primary Examiner* — David Naff
(74) *Attorney, Agent, or Firm* — Birch, Stewart, Kolasch & Birch, LLP

(57) ABSTRACT

To provide a new reductive-stimuli-responsive degradable gel that allows any control of decomposition of the three-dimensional base material for cell culture and production of a completely biological three-dimensional cellular structure consisting only of cells and cells-produced extracellular matrix and that allows safe recovery of the cellular structure produced. A stimuli-responsive hydrogel, characterized by being produced by crosslinking a water-soluble polymer with a compound having a disulfide bond in the molecular chain.

11 Claims, 7 Drawing Sheets

CONTROLLABLY DEGRADABLE HYDROGEL FOR CULTURING CELLS TO PRODUCE THREE-DIMENSIONALLY ORGANIZED CELLS

TECHNICAL FIELD

The present invention relates to a hydrogel, more specifically, to a reductive-stimuli-responsive degradable gel.

BACKGROUND ART

Currently, transplantation therapy and reconstructive surgical therapy are mainly practiced in surgical medicine, but there is a persistent problem of unavailability of sufficient donors, and these therapies have a larger load on patients and often demanded repeated surgery. For these reasons, a third therapy, i.e., regeneration therapy, is attracting attention and highly expected.

In organs relatively simpler in structure such as skin, bone, and cartilage, a culture method in combination of the stem cell in the patient's organ and a biodegradable base material is effective, and some of such methods are already in the phase of clinical test. However, the regeneration therapy for complicated body organs that are structured by various kinds of cells and an extracellular matrix and that demand supply of nutrition through the blood vessel, such as of liver, kidney and pancreas, are still in the basic research phase. One reason for the delay in research on complicated body organs is a problem in conversion of the cells into a three-dimensional structure.

Cell organization is a scientific region actively studied in the regeneration therapy field. Studies on cell organization are grossly grouped into studies on two-dimensional cell sheet by using a heat-sensitive-polymer-grafted culture dish and those on lamination of multiple kinds of cells. In Japan, Okano et al. of Tokyo Women's Medical Univ. are studying co-culture of vascular endothelial cell and hepatocyte cell by using a micropatterned graft surface of a heat-sensitive polymer and reported that it was possible to form a two-dimensional co-culture cell sheet (Non-patent Documents 1, 2 and 3). In abroad, Desai et al. in Boston University reported a three-dimensional cell organization of a laminate of three kinds of cells formed on the patterning surface of PDMS stamp (Non-patent Document 4).

However, it was not possible to achieve the three-dimensional organization by the cell sheet method, and, in the case of lamination only of cells, such as that reported by Desai et al., cell migration results in random mixing, non-control of organization. Recently, three-dimensional culture of cells in a revolving incubator is often carried out, but the cell proliferation leads to increase in cell density and also difficulty in supplying nutrients, causing a problem of death in internal cells. As described above, studies on three-dimensional organization of cells are still in the early basic research level, and there is currently no basic finding desirable for three-dimensional organization, and thus, there is an urgent need for a method to solve the problems.

On the other hand, studies on three-dimensional culture-organization by using a hydrogel (base material) of polylactic acid or collagen were actively in progress in the past ten years in Japan and abroad. These hydrogels have favorable cell adhesiveness, but the cells are grown too densely in the later phase of cell culture, resulting in inhibition of internal supply of nutrients by the dense network structure of hydrogel at the millimeter and micrometer level and thus, causing a problem of death of internal cells. Further, it is reported that polylactic acid hydrogels remain in the body as implanted for one year or more without decomposition, possibly causing inflammation and tumor generation. It is necessary to control the degradability of the base material to solve these problems.

However, up to now, there is no report on the method of controlling freely decomposition of the base material for a three-dimensional cell culture and constructing and safety collecting cellular structures.

Non-patent Document 1: Y. Tsuda et al., J. Biomed. Mater. Res. 69A, 70-78 (2004)

Non-patent Document 2: Y. Tsuda et al., Biomaterials 26, 1885-93 (2005)

Non-patent Document 3: A. Maya et al., Biomaterials 23, 1121-1130 (2002)

Non-patent Document 4: W. Tan. et al., Biomaterials 25, 1355 (2004)

DISCLOSURE OF INVENTION

Technical Problems to be Solved

An object of the present invention is to provide a new reductive-stimuli-responsive degradable gel that allows any control of decomposition of the three-dimensional base material for cell culture and production of a completely biological three-dimensional cellular structure consisting only of cells and cells-produced extracellular matrix and that allows safe recovery of the cellular structure produced.

Means to Solve the Problems

The present invention provides a stimuli-responsive hydrogel produced by crosslinking a water-soluble polymer with a compound having a disulfide bond in the molecular chain.

Effects of the Invention

The present invention provides a new stimuli-responsive hydrogel.

BEST MODE FOR CARRYING OUT THE INVENTION

Figure 1:
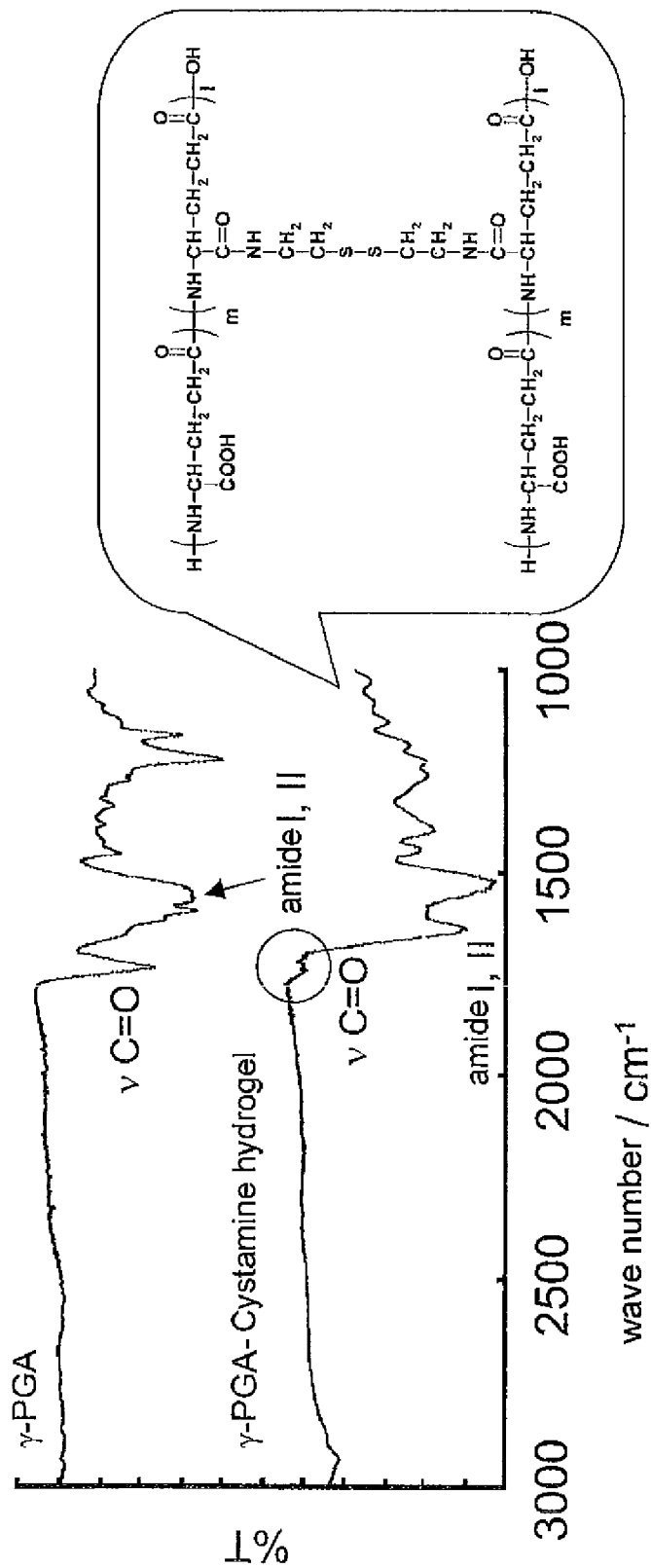
FIG. 1 is a FT-IR spectrum of a poly($\gamma$-glutamic acid)-cystamine hydrogel.

Examples of the water-soluble polymers for use in the present invention include polyamino acids, saccharides, polyesters, polyamides, polyethers, vinyl polymers, and the copolymers thereof. The "water solubility" is needed for solubilization of the polymer in the medium after decomposition. The molecular weight of the polymer is not particularly limited, if the polymer is water-soluble, but an excessively smaller molecular weight is unfavorable because it is not possible to produce a hydrogel superior in cell adhesiveness and convenience of operation.

Examples of the water-soluble polyamino acids include those having reactive functional groups such as —NH$_2$, —OH, or —COOH on the side chains and terminals, such as poly(γ-glutamic acid), poly(α-glutamic acid), poly(aspartic acid), poly(lysine), poly(arginine), poly(glutamine), poly(serine), poly(threonine), poly(tyrosine), the copolymers thereof, and the like.

Examples of the saccharides include those having reactive functional groups such as —CH$_2$OH, —COOH, or —NH$_2$, on the side chains and terminals such as glucose, cellulose, alginic acid, chitosan, hyaluronic acid, chondroitin sulfate, dermatan sulfate, heparin, the copolymers thereof, and the like.

Examples of the water-soluble polyesters include those having reactive functional groups such as NH$_2$, —OH, or —COOH on the side chains and terminals, such as polymalic acid, low-molecular-weight polylactic acid, low-molecular-weight polyglycol acid, low-molecular-weight poly-ε-caprolactone, and poly-β-hydroxybutyric acid.

Examples of the water-soluble polyamides include those having reactive functional groups such as NH$_2$, —OH, or —COOH on the side chains and terminals such as polymannaramide and polygalactoramide.

Examples of the water-soluble polyethers include those having reactive functional groups such as —NH$_2$, —OH, or —COOH on the terminals, such as polyethylene glycol and polypropylene glycol.

Examples of the water-soluble vinyl polymers include those having reactive functional groups such as —NH$_2$, —OH, or —COOH on the side chains, such as polyacrylic acid, polyvinylamine, polymethacrylic acid, and polyallylamine.

The water-soluble polymer is preferably a natural water-soluble polymer such as polyamino acids, saccharides, or polymalic acids, from the viewpoints of safety to cells such as toxicity after decomposition. It is particularly preferably a polyamino acid or a saccharide for easily production of the hydrogel without use of an organic solvent, and among polyamino acids, poly(ε-lysine) is selected from the viewpoint that it can be collected easily in a great amount from bacteria; and poly(γ-glutamic acid) is selected from the viewpoint that it is collected easily in a great amount from bacteria and is higher in molecular weight, which is advantageous for molding. Among saccharides, chitosan is selected from the viewpoint that it is prepared in a great amount by chemical treatment of chitin, a substance which is contained in the shell of shrimps and crabs, and alginic acid is selected from the viewpoint that it is contained in a great amount in sea weeds and collected in a great amount.

Examples of the "compound having a disulfide bond in the molecular chain" for use in the present invention (hereinafter, referred to simply as "crosslinking agent") include cystamine, cystine, 2-hydroxyethyldisulfide, 3,3'-dithiodipropionic acid (DTDP), glutathione disulfide, 3,3'-dithiopropiohydrazide, the derivatives thereof, and the like. Such a crosslinking agent is selected from the viewpoints of terminal reactive functional group and natural availability, and for example, cystamine is used favorably, because it has a terminal —NH$_2$ group and its decomposition products are also natural compounds.

Crosslinking of a water-soluble polymer with a crosslinking agent is carried out in reaction of the reactive functional group in the water-soluble polymer and the reactive functional group of the crosslinking agent. For example, the crosslinking of poly(γ-glutamic acid) with cystamine proceeds in aqueous solution in the following reaction: condensation of poly(γ-glutamic acid) side-chain —COOH groups with cystamine terminal —NH$_2$ groups, forming amide bonds. Crosslinking gives a hydrogel.

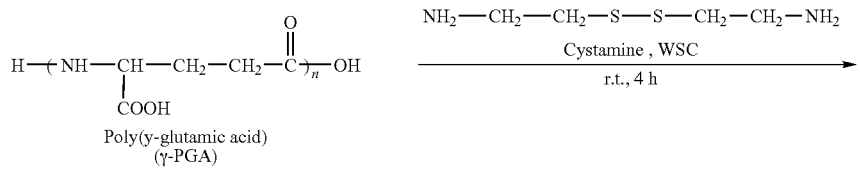

[Formula 1]

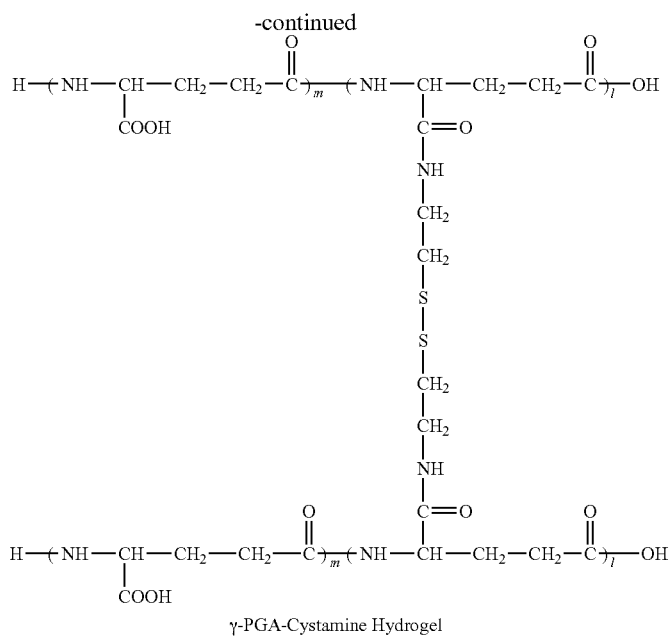

γ-PGA-Cystamine Hydrogel

A condensation agent, such as 1-ethyl-3-[3-(dimethylamino)propyl]carbodiimide (water-soluble carbodiimide: WSC) or N,N'-dicyclohexyl carbodiimide (DCC), may be used in an amount of about 1 to 10 moles with respect to 1 mole of cystamine during the reaction above.

The reaction temperature is 4 to 25° C., preferably 4° C., from the viewpoint for prevention of generation of by-products of the water-soluble carbodiimide and the reaction pressure may be atmospheric pressure.

Important in the reaction conditions are the concentration of the water-soluble polymer and the molar ratio of functional groups. It is because it is necessary to produce a hydrogel superior in cell adhesiveness and convenience of operation. For example during the crosslinking reaction shown in Formula 1, the concentration of poly(γ-glutamic acid) is 4 to 9 wt %, preferably 5 to 7 wt %. Too high concentration results in generation of a rigid hydrogel that is lower in the convenience of operation, while too low concentration causes a problem of difficulty in producing a self-supporting hydrogel.

As for the molar ratio of functional groups, the equivalence of the functional group in the crosslinking agent is preferably set to half or more of the equivalence of the functional group in the water-soluble polymer. An excessively smaller molar ratio causes a problem of difficulty in producing a self-supporting hydrogel.

The reaction can be terminated, if the solvent water does not flow out any more when the reaction container is placed tilted.

The reaction product may be washed with water and then stored in water, or may be dried for example by means of freeze drying. Preferably, it is stored in water.

The hydrogel according to the present invention characteristically should be degradable, in response to acidic pH or reducing agent.

The hydrogel obtained as described above is responsive to reductive stimuli. The term "reductive-stimuli-responsive" means that the polymer is degradable under reductive atmosphere or in response to a reducing agent and the decomposition is controllable. The decomposition rate of the hydrogel according to the present invention is controllable, according to the presence or absence or the concentration of a reducing agent over a period of several minutes to several days. The —S—S— bond present in the crosslinking agent is cleaved by the reducing agent, forming thiol groups.

Examples of the reducing agents for use include dithiothreitol (DTT), glutathione (GSH), dihydrolipoic acid (DHLA), β-mercaptoethanol, β-mercaptoethylamine, dithioerythritol, cysteine (Cys), and the like. It is possible to decompose only the hydrogel without damage on the cells proliferating therein, by using a reductive substance present in living organisms such as glutathione (GSH), dihydrolipoic acid (DHLA) or cysteine (Cys). Use of GSH, DHLA or Cys is preferable, from the viewpoint of the safety to cells.

The decomposition rate can be controlled properly by adjustment of the kinds of hydrogel and reducing agent, concentrations thereof, decomposition temperature and pressure, and others. For example, as shown in the Examples below, the decomposition rate of a poly(γ-glutamic acid)-cystamine hydrogel can be controlled in a range of several minutes to several days.

The stimuli-responsive poly(γ-glutamic acid)-cystamine hydrogel according to the present invention is suitable as a cell culture medium, and it is possible to proliferate various cells including human cells sufficiently and then decompose it, and thus to obtain a completely biological three-dimensional cellular structure consisting of the cells and the cell-produced extracellular matrix components such as collagen. It is also possible to obtain a cellular structure in the desired size and shape by modifying the shape of hydrogel. Because the decomposition products formed by the reductive reaction are polypeptides, the hydrogel is free from cell toxicity, bioabsorbable, and thus extremely safe. Needless to say, components need for cell proliferation such as fetal calf serum and others are normally contained in the cell culture medium.

Although the present invention was described mainly by taking a poly(γ-glutamic acid)-cystamine hydrogel as an example in the description above, other hydrogels would also be formed similarly and the degradability thereof can be controlled by those who are skilled in the art without any difficulty with reference to the description above and the Examples below.

Other applications thereof include pharmaceutical- and gene-releasing carriers, bone-regenerating materials, dental materials, separation film materials, base materials for inducing regeneration of tissues and organs in living bodies, and the like.

EXAMPLES

Preparative Examples 1 to 5

Preparation of poly(γ-glutamic acid)-cystamine Hydrogel

Poly(γ-glutamic acid) (γ-PGA) (645 mg (5 unit mmol)) was dissolved in 10 mL of 0.5 M aqueous sodium bicarbonate solution at the concentration (wt %) shown in the following Table 1; 776 mg (5 mmol) of a water-soluble carbodiimide (WSC: condensation agent) was added thereto; and the mixture was stirred at 4° C. for 15 minutes. Cystamine (563 mg (2.5 mmol)) was added thereto as a crosslinking agent; the solution obtained after stirring for several minutes was poured into the space having a thickness of 1 mm between two glass plates that were bound to each other via a silicone rubber, and allowed to react at room temperature for 3 hours. After reaction, the hydrogel obtained was washed with ultra-

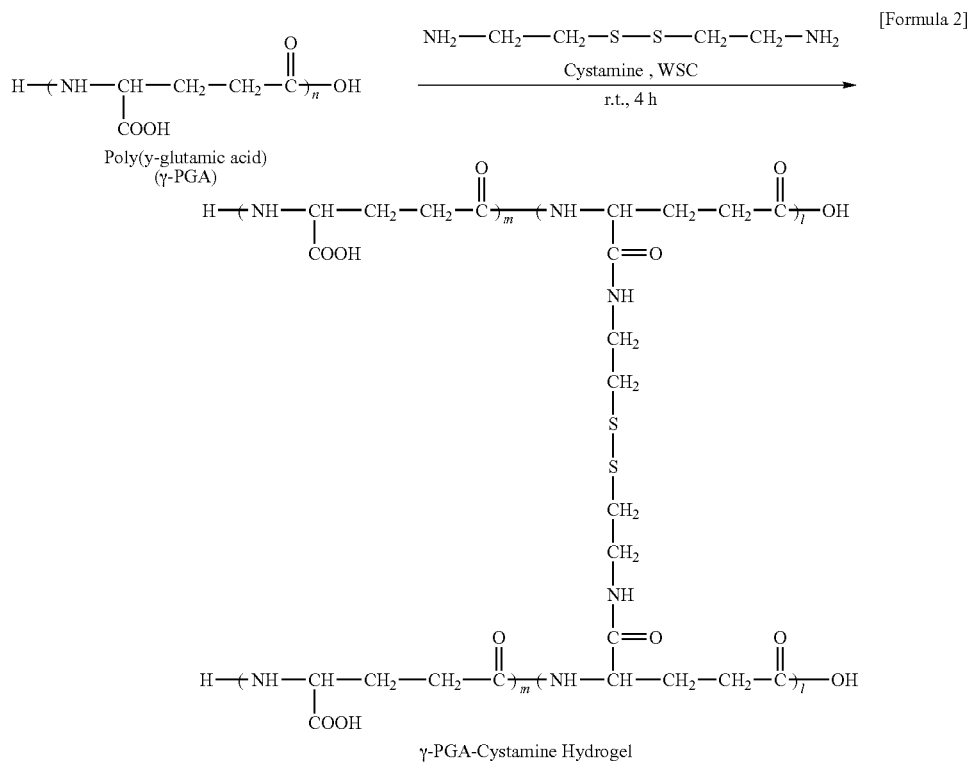

[Formula 2]

γ-PGA-Cystamine Hydrogel pure water for 4 hours and cut into disks having a diameter of 1 cm for evaluation. The evaluation will be described below.

TABLE 1

| Preparation | γ-PGA Concentration (wt %) | (unit mmol) | (mg) | WSC (mmol) | (mg) | Systamine (mmol) | (mg) | [NH$_2$]/ [COOH] | Swelling ratio[1] |
|---|---|---|---|---|---|---|---|---|---|
| 1 | 3.0 | 5.0 | 645 | 5.0 | 776 | 2.5 | 563 | 1.0 | —[3] |
| 2 | 5.0 | 5.0 | 645 | 5.0 | 776 | 2.5 | 563 | 1.0 | 110 |
| 3 | 6.0 | 5.0 | 645 | 5.0 | 776 | 2.5 | 563 | 1.0 | 25 |
| 4 | 7.0 | 5.0 | 645 | 5.0 | 776 | 2.5 | 563 | 1.0 | 7.0 |
| 5 | 10 | 5.0 | 645 | 5.0 | 776 | 2.5 | 563 | 1.0 | —[2] |
| 6 | 3.0 | 5.0 | 645 | 5.0 | 776 | 5.0 | 1126 | 2.0 | — |
| 7 | 5.0 | 5.0 | 645 | 5.0 | 776 | 5.0 | 1126 | 2.0 | 5.0 |
| 8 | 6.0 | 5.0 | 645 | 5.0 | 776 | 5.0 | 1126 | 2.0 | 39 |
| 9 | 7.0 | 5.0 | 645 | 5.0 | 776 | 5.0 | 1126 | 2.0 | 31 |

[1]Swelling rate = (Ws − Wd)/Wd, Ws: weight of swollen hydrogen, and Wd: weight of dry hydrogel
[2]No gelation possible under the same condition, because of excessively high gelation speed.
[3]"—" indicates that no self-supportive hydrogel was obtained.

The FT-IR (Fourier transform infrared absorption) spectrum of the hydrogel obtained in Preparative Example 3 is shown in FIG. 1.

The peak (vC=O) derived from the carbonyl of the carboxyl group in the poly(γ-glutamic acid) became smaller and the shape of the amide II peak changed after crosslinking with cystamine, indicating that the carboxyl groups of poly(γ-glutamic acid) were converted to amide groups, i.e., that the poly(γ-glutamic acid) was crosslinked with cystamine.

Preparative Examples 6 to 9

A disk-shaped hydrogel was prepared in a manner similar to Preparative Example 1, except that the cystamine concentration was changed to 1126 mg (5.0 mmol) and γ-PGA was dissolved at the concentration shown in Table 1, and evaluated similarly.

Preparative Example 10 to 14

Preparation of poly(γ-glutamic acid)-cystine Hydrogel

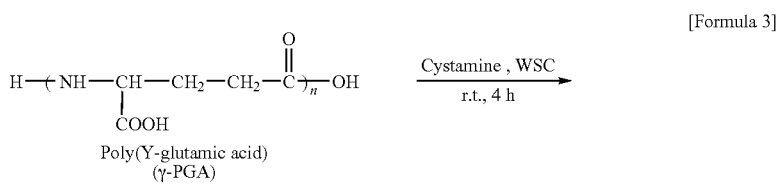

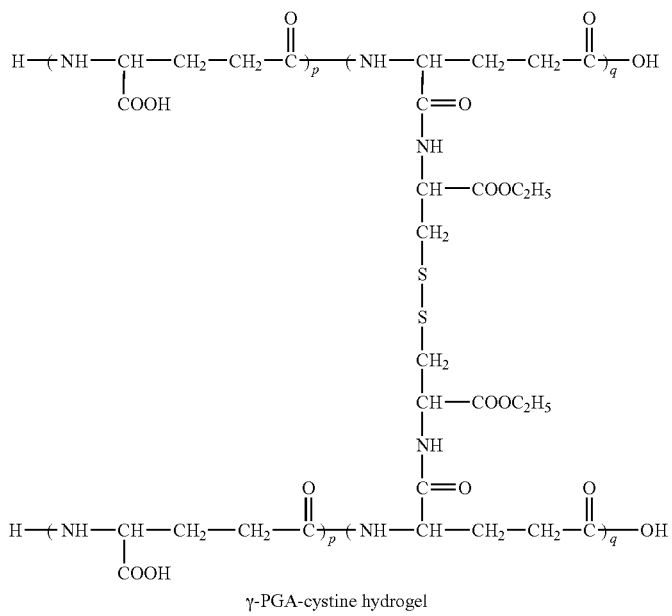

γ-PGA-cystine hydrogel

Gamma (γ)-PGA (645 mg (5 unit mmol)) was dissolved in mL of 0.5 M aqueous sodium bicarbonate solution at the concentration (wt %) shown in the following Table 2; 776 mg (5 mmol) of a water-soluble carbodiimide (WSC: condensation agent) was added thereto; and the mixture was stirred at 4° C. for 15 minutes. Cystamine (923 mg (2.5 mmol)) was added thereto as a crosslinking agent; the solution obtained after stirring for several minutes was poured into the space having a thickness of 1 mm between two glass plates that were bound to each other via a silicone rubber, and allowed to react at room temperature for 3 hours. After reaction, the hydrogel obtained was washed with ultrapure water for 4 hours and cut into disks having a diameter of 1 cm for evaluation.

TABLE 2

| Preparation | Concentration (wt %) | γ-PGA (unit mmol) | γ-PGA (mg) | WSC (mmol) | WSC (mg) | Cystine (mmol) | Cystine (mg) | [NH$_2$]/ [COOH] | Swelling ratio[1] |
|---|---|---|---|---|---|---|---|---|---|
| 10 | 3.0 | 5.0 | 645 | 5.0 | 776 | 2.5 | 563 | 1.0 | —[2] |
| 11 | 5.0 | 5.0 | 645 | 5.0 | 776 | 2.5 | 563 | 1.0 | 200 |
| 12 | 6.0 | 5.0 | 645 | 5.0 | 776 | 2.5 | 563 | 1.0 | 13 |
| 13 | 7.0 | 5.0 | 645 | 5.0 | 776 | 2.5 | 563 | 1.0 | 5.0 |
| 14 | 7.0 | 5.0 | 645 | 5.0 | 776 | 1.3 | 282 | 0.5 | 74 |

[1] Swelling rate = (Ws − Wd)/Wd, Ws: weight of swollen hydrogen, and Wd: weight of dry hydrogel
[2] "—" indicates that no self-supportive hydrogel was obtained.

Hydrogel Decomposition Test

The decomposition mechanism of the poly(γ-glutamic acid)-cystamine hydrogel is shown below.

Decomposition Mechanism by DTT

[Formula 4]

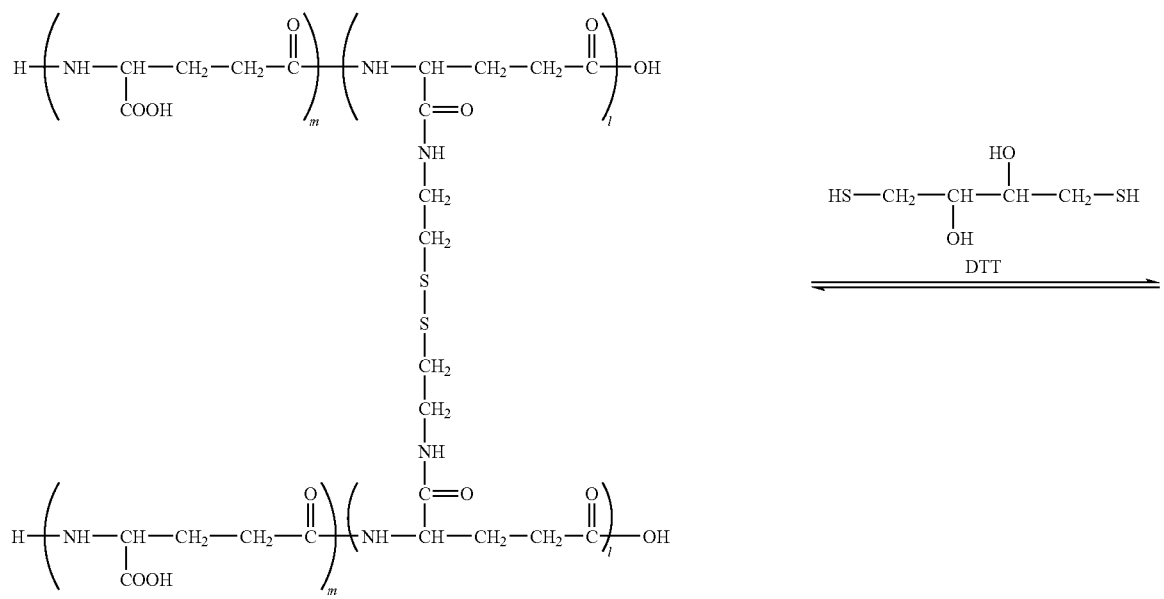

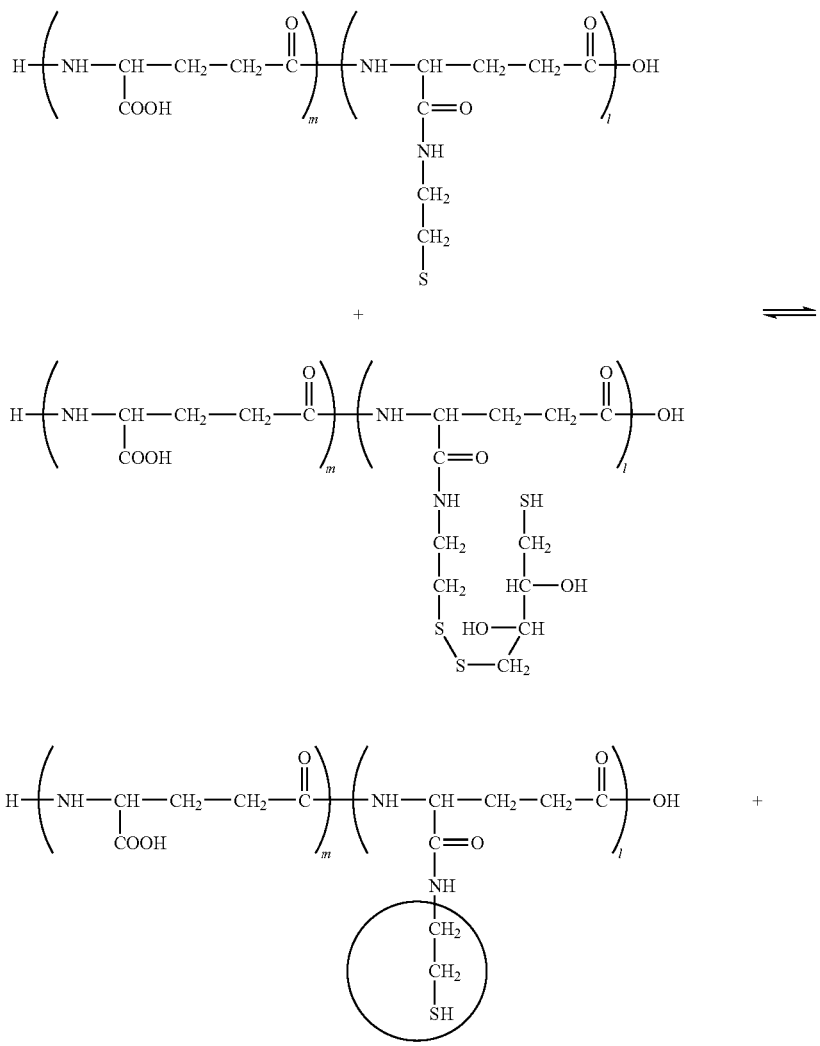

Each of the gels obtained in Preparative Examples 2, 3, 4, 12, and 13 and the gels after freeze drying was immersed in 50 mL of ultrapure water (milliQ water, manufactured by Millipore), phosphate buffered physiological saline (PBS), and a cell culture medium (containing 10% fetal calf serum) (Eagle's MEM (EMEM): manufactured by Nissui Pharmaceutical Co., Ltd.), and the period needed for decomposition was determined. The period needed for decomposition is a period until there was no residual gel confirmed by visual observation.

Because the decomposition test is an experiment significantly influenced by crosslinking density, samples similar in swelling degree (Preparative Examples 7, 8, 9, 11, and 14) and samples not forming a suitable gel (Preparative Examples 1, 5, 6, and 10) were not used in this experiment.

The gels were immersed in a cell culture medium of ultrapure water, PBS, containing 25 mM dithiothreitol (DTT) or 1.0 mM glutathione (GSH) as reducing agents, and the period needed for decomposition was determined. The change in gel weight by decomposition was determined by separating the gel from the solution after a specified time, wiping off excessive water thereon with Kimwipe (made by Nippon Paper Crecia Co., Ltd.), and measuring the weight of the gel. Results are summarized in the following Table 3.

Figure 2:
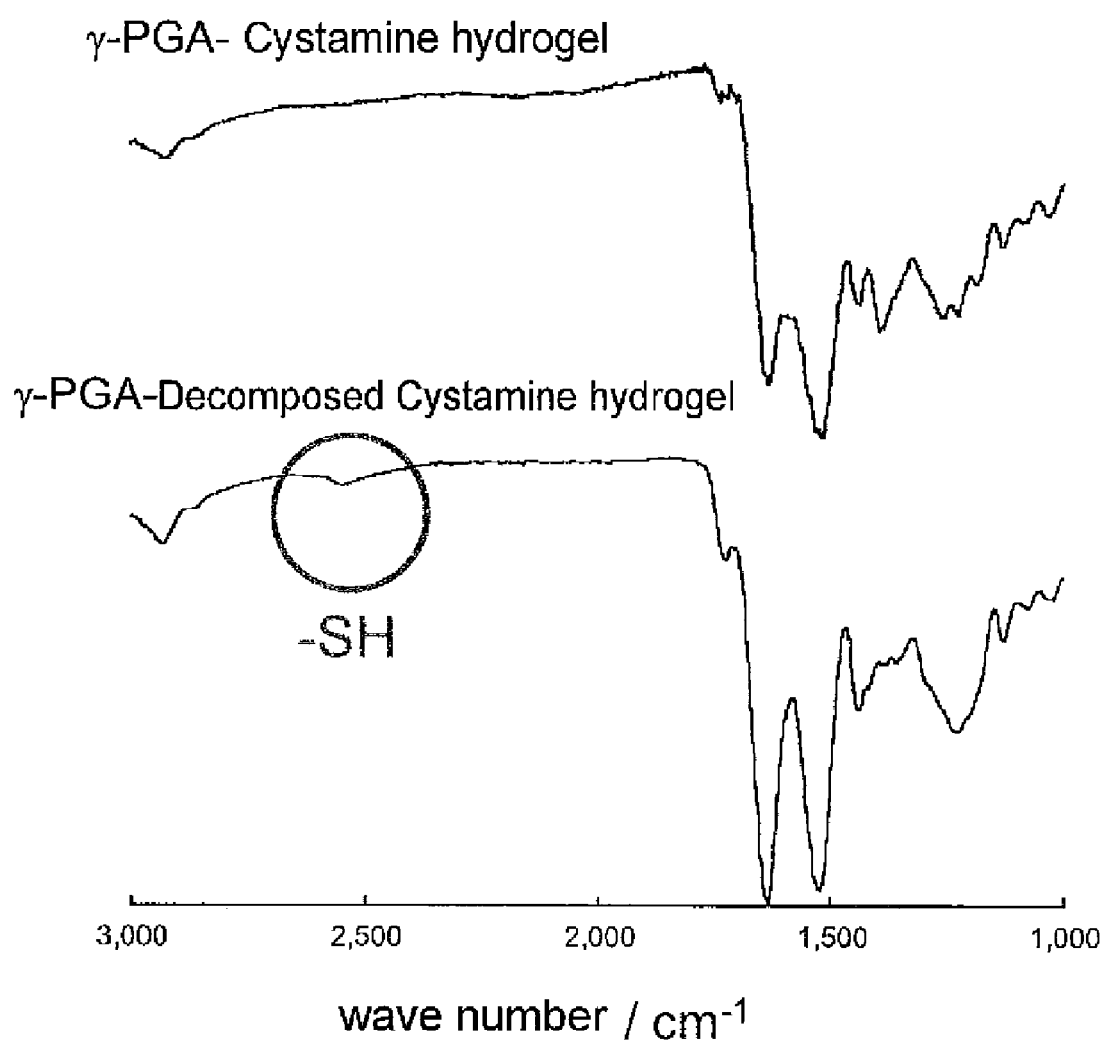
FIG. 2 is a FT-IR spectrum of a poly($\gamma$-glutamic acid)-cystamine hydrogel and the decomposition products thereof.
Figure 3:
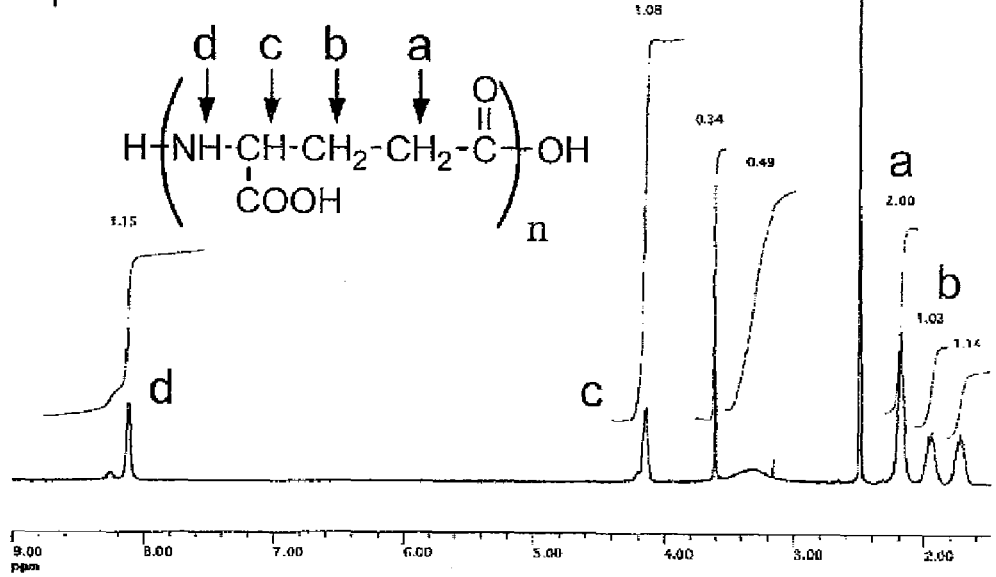
FIG. 3 is a $^1$H-NMR spectrum of a poly($\gamma$-glutamic acid)-cystamine hydrogel and the decomposition products thereof.
Figure 3:
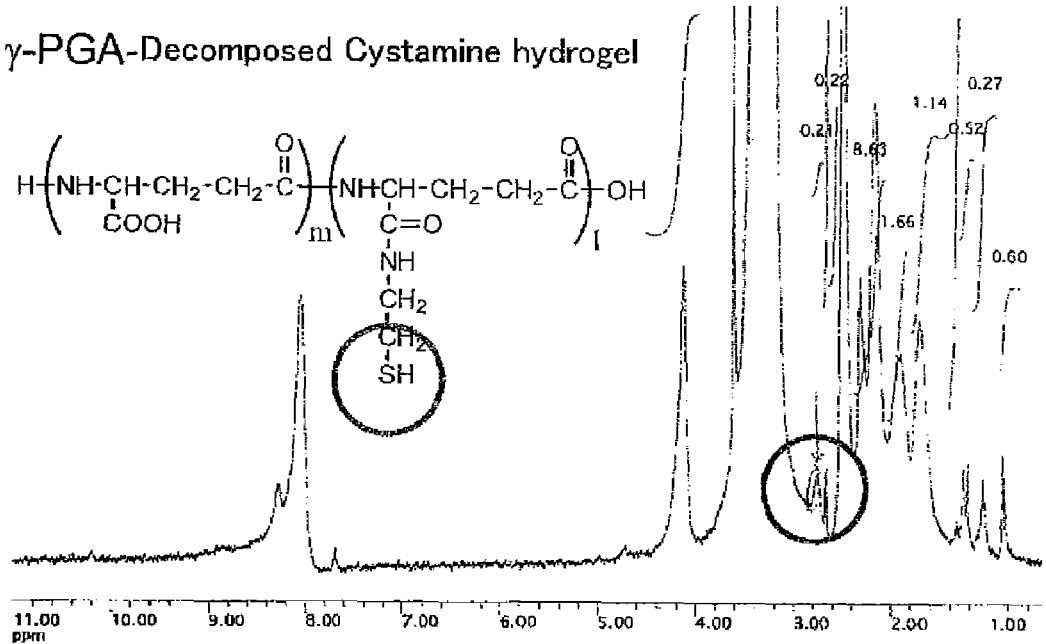

FIG. 2 shows a FT-IR spectrum (upper) of the poly(γ-glutamic acid)-cystamine hydrogel obtained in Preparative Example 3 and a FT-IR spectrum (lower) of the decomposition product obtained by decomposition of the gel with DTT by the method above. FIG. 3 shows a $^1$H-NMR spectrum (upper) of the poly(γ-glutamic acid)-cystamine hydrogel obtained in Preparative Example 3 and a $^1$H-NMR spectrum (lower) of the decomposition product obtained by decomposition of the gel with DTT by the method above.

In the FT-IR spectrum of FIG. 2, a peak of thiol group, which was not detected in the poly(γ-glutamic acid)-cystamine hydrogel, was observed at around 2500 cm$^{-1}$ in the decomposition product. It is known that no disulfide bond is detected in IR spectra. The results indicate that the disulfide bonds in the poly(γ-glutamic acid)-cystamine hydrogel were decomposed to thiol groups with DTT.

In the $^1$H-NMR spectrum of the decomposition product of poly(γ-glutamic acid)-cystamine hydrogel shown in FIG. 3, a thiol group-derived peak was detected at 2.8 ppm. The result indicates that the disulfide bonds in the poly(γ-glutamic acid)-cystamine hydrogel were decomposed to thiol groups with DTT.

TABLE 3

| Cross-linking Agent | Condition | Temperature[1] | milliQ | PBS | EMEM | DTT(25 mM) milliQ | DTT(25 mM) PBS | DTT(25 mM) EMEM | GHS(1 mM) milliQ | GHS(1 mM) PBS | GHS(1 mM) EMEM |
|---|---|---|---|---|---|---|---|---|---|---|---|
| Cystamine | wet gel | 5 wt % | —[2] | 50 h | 23 h | 0.75 h | 0.50 h | 0.50 h | — | 8.0 h | 4.5 h |
| | | 6 wt % | — | — | 80 h | 4.0 h | 1.5 h | 1.5 h | — | 45 h | 20 h |
| | | 7 wt % | — | — | — | 14 h | 14 h | 3.5 h | — | — | — |
| | dry gel | 5 wt % | — | — | 5.5 days | 15 h | 0.75 h | 3.0 h | 15 h | 36 h | 20 h |
| | | 6 wt % | — | — | — | 15 h | 2.5 h | 3.0 h | 15 h | 48 h | 28 h |
| | | 7 wt % | — | — | 7.0 days | 14 h | 3.5 h | 3.0 h | — | 73 h | 20 h |
| Csytine | wet gel | 6 wt % | — | — | — | 18 h | 3.0 h | 4.5 h | — | — | — |
| | | 7 wt % | — | — | — | — | 18 h | 17 h | — | — | — |
| | dry gel | 6 wt % | — | — | — | 4.5 h | 4.0 h | 12 h | — | — | — |

[1] γ-PGA concentration when the hydrogel was prepared
[2] "—" indicates that no decomposition occurred even after one week.

As shown in Table 3, the decomposition rate of the hydrogel according to the present invention can be controlled in the range of several minutes to several days, for example by presence or absence of a reducing agent such as DTT or GSH and adjustment of the concentration thereof. Presence of a reducing agent such as DTT or GSH leads to acceleration of the decomposition rate. The decomposition proceeds quite slowly in the EMEM medium, which contains an extremely trace amount of GSH. No decomposition occurs at all in ultrapure water (milliQ water).

Preparation of alginic acid-cystamine Hydrogel

[Formula 5]

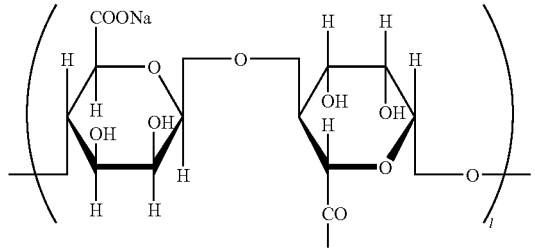

Alginic Acid (Alg)

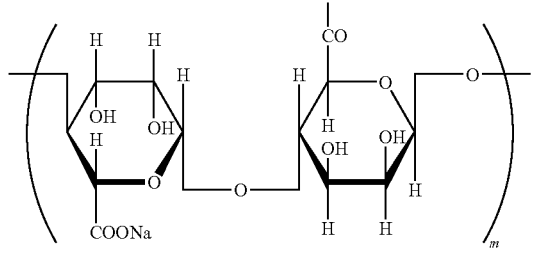

Alg-Cystamine hydrogel

Alginic acid (Alg) (452 mg (1 unit mmol)) was dissolved in 8.59 mL of 0.5 M aqueous sodium bicarbonate solution at a concentration of 5 wt %; 310 mg (2 mmol) of a water-soluble carbodiimide (WSC: condensation agent) was added thereto; and the mixture was stirred at room temperature for 15 minutes. Cystamine (225 mg (1 mmol)) was added as a crosslinking agent, and the solution obtained after stirring for several minutes was poured into the space having a thickness of 2 mm between two glass plates that were bound to each other via a silicone rubber, and allowed to react at room temperature for 24 hours. After reaction, the hydrogel obtained was washed with ultrapure water for 48 hours and cut into disks having a diameter of 1 cm for evaluation.

Figure 4:
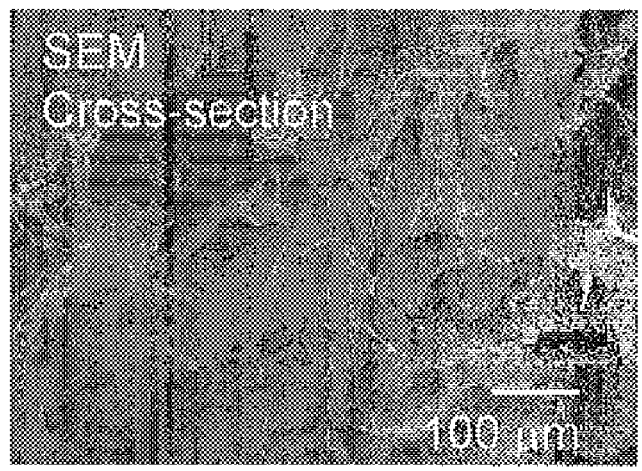
FIG. 4 is a scanning electron micrograph of a freeze-dried alginic acid-cystamine hydrogel.

A scanning electron micrograph of the alginic acid-cystamine hydrogel obtained after freeze drying is shown in FIG. 4.

The gel obtained by the preparative method above and the gel after freeze drying were immersed in 50 mL of ultrapure water containing 25 mM dithiothreitol (DTT) as a reducing agent, and the decomposition process was observed. The period needed for decomposition was 60 minutes. The period needed for decomposition is a period until there was no residual gel confirmed by visual observation.

Preparation of chitosan-dithiobispropionic acid Gel

[Formula 6]

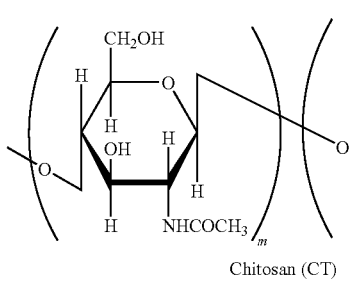
Chitosan (CT)

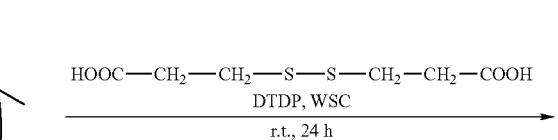

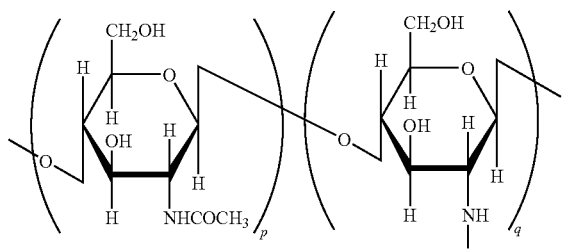

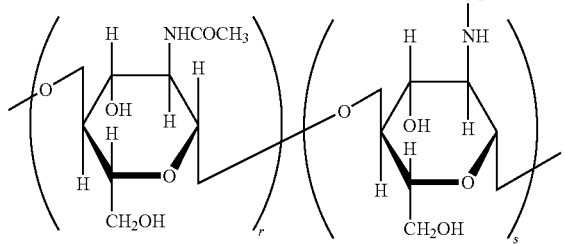
CT-Dithiobispropionic acid Gell

Chitosan (95 mg (0.5 unit mmol)) was dissolved in 9.4 mL of ultrapure water containing 61 mg (0.4 mmol) of 1-hydroxy-1H-benzotriazole (HOBt) (needed for solubilization of chitosan) at a concentration of 0.5 wt %. Aqueous sodium bicarbonate solution (0.5 M) (6.3 mL) containing 210 mg (1 mmol) of dithiobispropionic acid (DTDP) and 310 mg (2 mmol) of WSC and the aqueous chitosan solution were mixed; the solution obtained after stirring for several minutes was poured into the space having a thickness of 2 mm between two glass plates that were bound to each other via a silicone rubber, and allowed to react at room temperature for 24 hours. The hydrogel obtained was washed with ultrapure water for 48 hours and cut into disks having a diameter of 1 cm.

Preparation of ε-polylysine-dithiobispropionic acid Gel

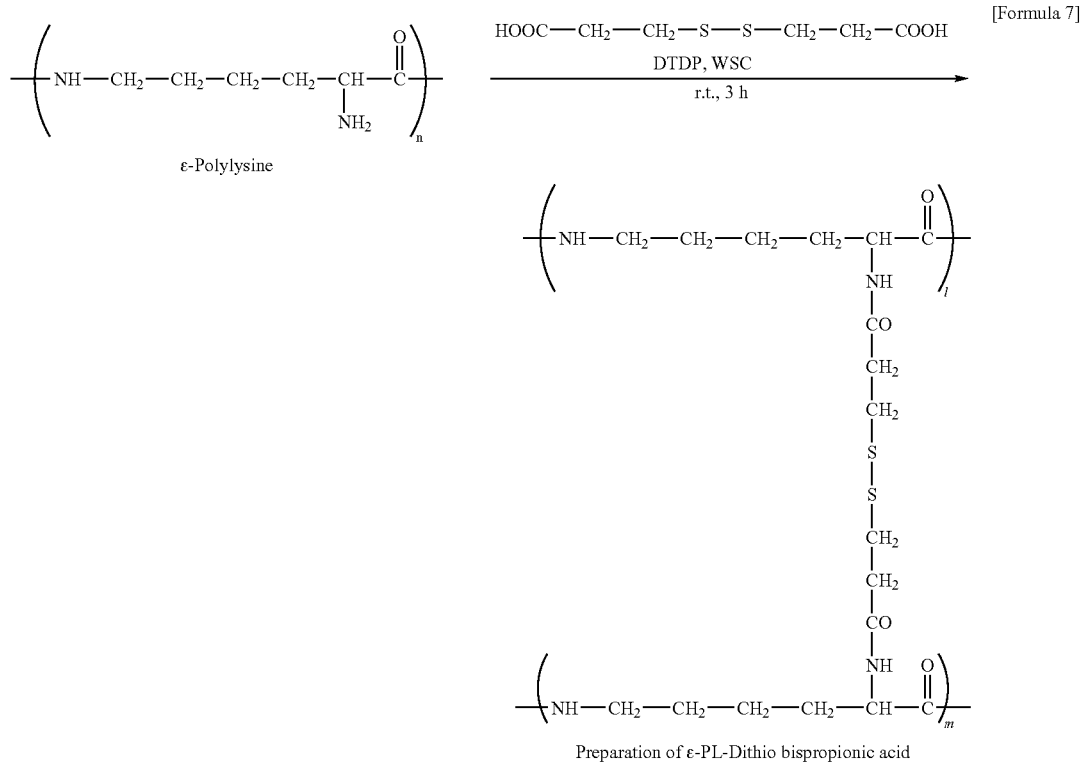

Preparation of ε-PL-Dithio bispropionic acid

Epsilon (ε)-polylysine (ε-PL) (164 mg (1 unit mmol)) was dissolved in 0.57 mL of 0.5 M aqueous sodium bicarbonate solution. Aqueous sodium bicarbonate solution (0.5 M) (2 mL) containing 105 mg (0.5 mmol) of DTDP and 155 mg (1 mmol) of WSC and the aqueous ε-PL solution were mixed; the solution obtained after stirring for several minutes was poured into the space having a thickness of 2 mm between two glass plates that were bound to each other via a silicone rubber, and allowed to react at room temperature for 3 hours. The hydrogel obtained was washed with ultrapure water for 48 hours and cut into disks having a diameter of 1 cm.

Figure 5:
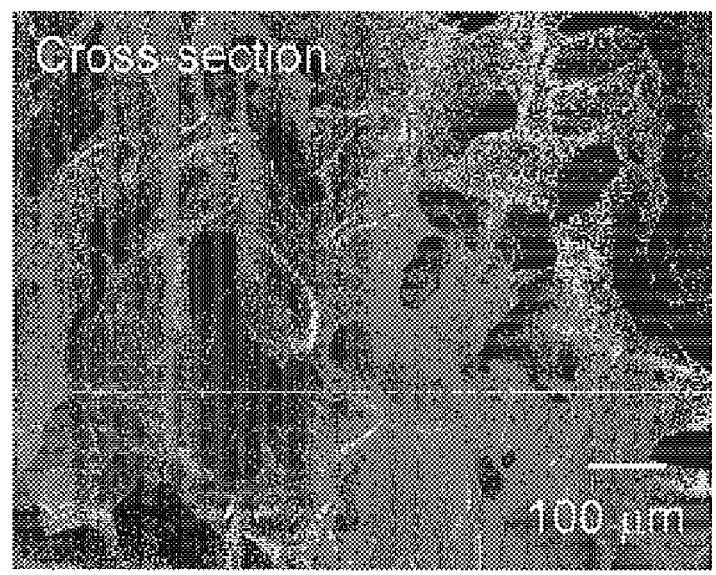
FIG. 5 is a scanning electron micrograph of a freeze-dried $\epsilon$-polylysine dithiobispropionic acid gel.

A scanning electron micrograph of the ε-polylysine dithiobispropionic acid gel obtained after freeze drying is shown in FIG. 5.

Cell Culture on Hydrogel and Decomposition of Hydrogel with GSH

Presence of Cell Sheet

The cystamine-crosslinked hydrogel prepared at a γ-PGA concentration of 6 wt % (Preparative Example 3) was immersed in a cell culture medium (containing 10% fetal calf serum) for 30 minutes, allowing substitution of water in the hydrogel with the medium. Then, the gel was placed on a 24-well multiplate; 1.0×10⁶ mouse L929 fibroblasts were inoculated on the hydrogel; 2 mL of the medium was added; and the mixture was cultured in an incubator at 37° C. and 5% $CO_2$ for one week. The medium was replaced with new medium every two days during culture.

After a week, the medium was removed, and the gel was immersed in a medium containing 1 mM GSH for six hours, allowing decomposition only of the hydrogel. The cells on the hydrogel and the cell sheet recovered after gel decomposition was analyzed under a phase-contrast microscope.

In addition, the cell sheet obtained was cultured in a tissue culture polystyrene dish (TCPS) for three days, showing migration of the cells from the cell sheet to TCPS, which indicates that the cell sheet obtained is alive.

Preparation of Three-Dimensional Cellular Structure

Figure 6:
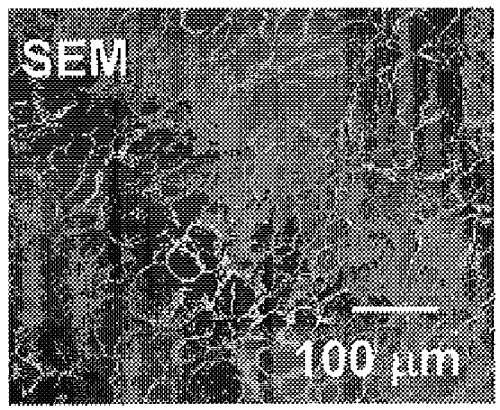
FIG. 6 is a scanning electron micrograph of a freeze-dried poly($\gamma$-glutamic acid)-cystamine hydrogel (before cell culture).

Poly(γ-glutamic acid) (γ-PGA) (645 mg (5 unit mmol)) was dissolved in 10 mL of 0.5 M aqueous sodium bicarbonate solution at a concentration of 6 wt %; 776 mg (5 mmol) of a water-soluble carbodiimide (WSC: condensation agent) was added thereto; and the mixture was stirred at 4° C. for 15 minutes. Cystamine (563 mg (2.5 mmol)) was added as a crosslinking agent, and the solution obtained after stirring for several minutes was poured into the space having a thickness of 2 mm between two glass plates that were bound to each other via a silicone rubber, and allowed to react at room temperature for 24 hours. After reaction, the hydrogel obtained was washed with ultrapure water for 48 hours and cut into disks having a diameter of 1 cm, and the disks were freeze dried for 3 days. Results of scanning electron microscope (SEM) observation of the gel obtained are shown in FIG. 6 (before culture).

The hydrogel after freeze drying was immersed in a cell culture medium (containing 10% fetal calf serum) for 30 minutes. Then, the gel was placed on a 6-well multiplate; 1.0×10⁶ mouse L929 fibroblasts were inoculated on the hydrogel; 5 mL of the medium was added; and the mixture was cultured in an incubator at 37° C. and 5% $CO_2$ for ten days. The medium was replaced with new medium every two days during culture.

Figure 7:
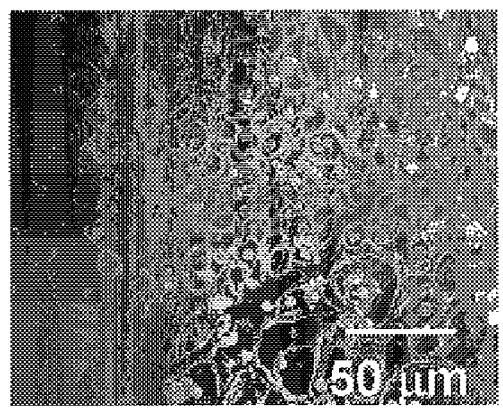
FIG. 7 is a scanning electron micrograph of the poly($\gamma$-glutamic acid)-cystamine hydrogel (after cell culture).

A SEM micrograph of the gel after culture for ten days is shown in FIG. 7. The results by SEM observation showed invasion of cells into the pores inside the gel.

The medium was removed after ten days, and the gel was immersed in 50 mL of a medium containing 5 mM cysteine for 12 hours, allowing decomposition only of the hydrogel.

Decomposition only of the get gave a cellular structure that was transcribed from the gel form, having a diameter of 1 cm and a thickness of 2 mm. SEM micrographs of the cellular structure containing the cells obtained by the decomposition and the extracellular matrix produced by the cells are shown in FIG. 8.

Figure 8:
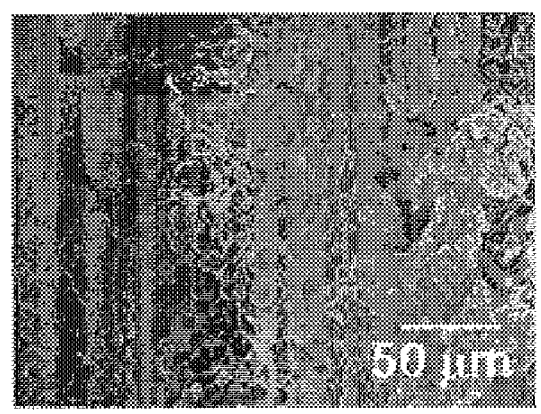
FIG. 8 is a scanning electron micrograph of a three dimensional cellular structure obtained by cell culture.

The micrograph of FIG. 8 shows that each cell has a size of approximately 10 μm. The cells should be present densely in the length and width directions, for the cells of 10 μm in diameter to form a cellular structure having a diameter of 1 cm and a thickness of 2 mm. Two hundred (200) cells should be aligned in the vertical direction, simply for them to form a layer having a thickness of 2 mm. It is actually impossible for the cells to form the cellular structure having a diameter of 1 cm and a thickness of 2 mm that is separated from the gel, indicating that the cells are present densely packed three-dimensionally together with the collagen component produced by the cells. The electron micrograph in FIG. 8 shows that the cells are aligned both in the length and width directions, distinctively indicating production of a cellular structure wherein cells are aligned three-dimensionally.

Evaluation of the Residue of Hydrogel Decomposition Components by Using a Fluorescence-Labeled Hydrogel after Three-Dimensional Cellular Structure is Formed (Preparation of Fluorescence-Labeled γ-PGA)

Poly(γ-glutamic acid) (γ-PGA) (20 mg (156 unit μmol)) was dissolved in 10 mL of 0.5 M aqueous sodium bicarbonate solution; 1.0 mg (644 μmol) of a water-soluble carbodiimide (WSC: condensation agent) was added thereto; and the mixture was stirred at 4° C. for 15 minutes. A fluorescent reagent, Alexa Fluor 488 cadaverine sodium salt of 1 mg (1.56 μmol), was added thereto in the dark, and the mixture was allowed to react at 4° C. for 1 hour and additionally at room temperature for 24 hours. After reaction, the product was purified by dialysis against ultrapure water for 3 days in the dark and freeze dried for 3 days in the dark, to give a fluorescence-labeled γ-PGA.

(Fluorescence-Labeled Gel and Cell Culture)

Figure 9:
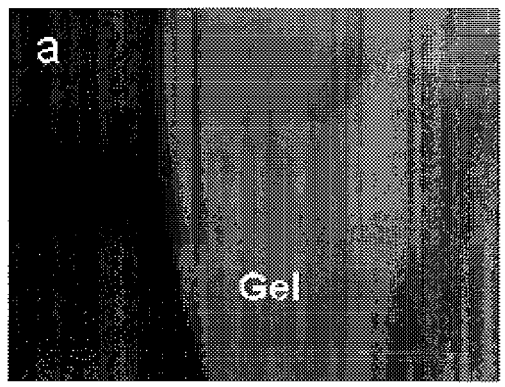
FIG. 9 is a fluorescence micrograph of a fluorescence-labeled poly($\gamma$-glutamic acid)-cystamine hydrogel (before cell culture).

Fluorescence-labeled γ-PGA (7 mg) (0.05 unit μmol) and 638 mg (4.95 unit μmol) of poly(γ-glutamic acid) (γ-PGA) were dissolved in 10 mL of 0.5 M aqueous sodium bicarbonate solution at a concentration of 6 wt %; 776 mg (5 mmol) of a water-soluble carbodiimide (WSC: condensation agent) was added thereto; and the mixture was stirred in the dark at 4° C. for 15 minutes. Cystamine (563 mg (2.5 mmol)) was added thereto as a crosslinking agent; the solution obtained after stirring for several minutes was poured into the space having a thickness of 2 mm between two glass plates that were bound to each other via a silicone rubber, and allowed to react at room temperature for 24 hours in the dark. After reaction, the hydrogel obtained was washed with ultrapure water for 48 hours and cut into disks having a diameter of 1 cm, and the disk was freeze-dried for 3 days. The fluorescence micrograph of the gel before cell culture is shown in FIG. 9.

Figure 10:
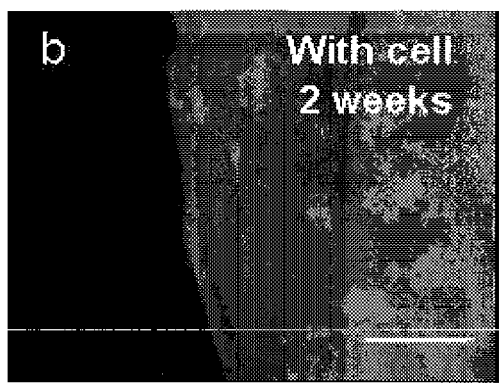
FIG. 10 is a fluorescence micrograph of the fluorescence-labeled poly($\gamma$-glutamic acid)-cystamine hydrogel (after cell culture).
Figure 11:
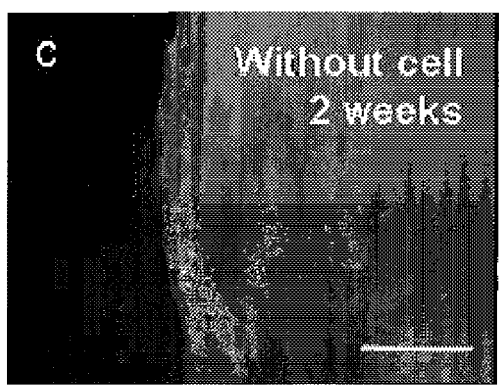
FIG. 11 is a fluorescence micrograph of a fluorescence-labeled poly(γ-glutamic acid)-cystamine hydrogel (after culture without cell inoculation).

The fluorescence-labeled gel was immersed in the cell culture medium (containing 10% fetal calf serum) for 30 minutes. Then, the gel was placed on a 6-well multiplate; $1.0 \times 10^6$ mouse L929 fibroblasts were inoculated thereon; 5 mL of the medium was added; and the mixture was cultured in an incubator at 37° C. and 5% $CO_2$ for 2 weeks. The medium was replaced with new medium every two days during the culture. The fluorescence micrograph of the gel after culture for two weeks is shown in FIG. 10. For comparison, the fluorescence micrograph of the gel incubated under the same condition for 2 weeks in the medium without inoculation of the cells is shown in FIG. 11.

(Decomposition of Fluorescence-Labeled Gel after Cell Culture)

Figure 12:
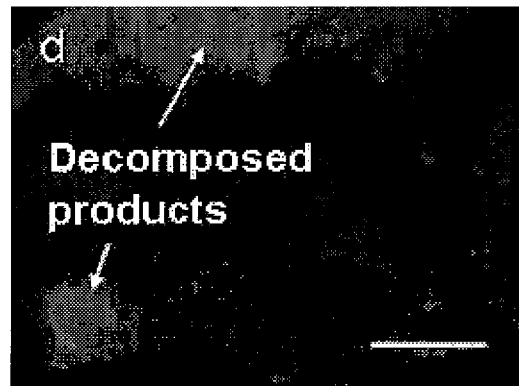
FIG. 12 is a fluorescence micrograph showing the cellular structure of the fluorescence-labeled poly(γ-glutamic acid)-cystamine hydrogel after decomposition and washing once.
Figure 13:
FIG. 13 is a fluorescence micrograph showing the cellular structure of the fluorescence-labeled poly(γ-glutamic acid)-cystamine hydrogel after decomposition and repeated washing for five times.
Figure 14:
FIG. 14 is a phase-contrast micrograph showing the cellular structure of the fluorescence-labeled poly(γ-glutamic acid)-cystamine hydrogel after decomposition and repeated washing for five times.

Two weeks later, the medium was removed; the gel was immersed in 50 mL of a medium containing 5 mM cysteine for 12 hours, allowing decomposition only of the hydrogel. The fluorescence micrograph of the structure obtained by the decomposition after washing with phosphate buffered physiological saline (PBS) after 12 hours is shown in FIG. 12. Observation of some fluorescence indicates residual of the decomposition products. Then, the fluorescence micrograph of the gel after washing five times with PBS and the phase-contrast micrograph at the same position are shown in FIGS. 13 and 14. Observation of no fluorescence at the position where the structure is observed under phase-contrast microscope indicates that the decomposition product had been completely removed.

INDUSTRIAL APPLICABILITY

The stimuli-responsive hydrogel according to the present invention, which gives a completely biological three-dimensional cellular structure consisting of cells and cell-derived extracellular matrix and being able to be collected safely, is applicable in the field of regeneration medicine.

In addition, the stimuli-responsive hydrogel according to the present invention is also environmentally safe, and thus, can also be used in the environmental field, for example, as a moisturizer.

The invention claimed is:

1. A material for culturing cells to produce three-dimensionally organized cells, comprising a hydrogel produced by crosslinking a water-soluble poly(γ-glutamic acid) at a concentration of 4 to 9 wt % with a crosslinking compound having a disulfide bond in the molecular chain at an equivalence of functional group in the crosslinking compound of half or more of the equivalence of functional group in the water-soluble poly(γ-glutamic acid);

wherein the hydrogel is capable of being controllably decomposed under a reductive atmosphere or in response to a reducing agent to separate three-dimensionally organized cells having a three-dimensional cellular structure consisting of cells and cell-produced extracellular matrix.

2. A method for producing three-dimensionally organized cells, comprising;

culturing cells with a material for culturing to produce three-dimensionally organized cells comprising a hydrogel produced by crosslinking a water-soluble poly (γ-glutamic acid) at a concentration of 4 to 9 wt % with a crosslinking compound having a disulfide bond in the molecular chain at an equivalence of functional group in the crosslinking compound of half or more of the equivalence of functional group in the water-soluble poly(γ-glutamic acid), controllably decomposing the stimuli-responsive hydrogel with a reducing agent, and separating the three-dimensionally organized cells from the material, to separate the three-dimensionally organized cells having a three-dimensional cellular structure consisting of cells and cell-produced extracellular matrix.

3. The method according to claim 2, wherein the reducing agent is glutathione (GSH), dihydrolipoic acid (DHLA) or cysteine (Cys).

4. The material according to claim 1, wherein the compound having a disulfide bond in the molecular chain is cystamine, cystine or 3,3'-dithiodipropionic acid.

5. The material according to claim 1, wherein the compound having a disulfide bond in the molecular chain is cystamine or cystine.

6. The method according to claim 2, wherein the compound having a disulfide bond in the molecular chain is cystamine, cystine or 3,3'-dithiodipropionic acid.

7. The method according to claim 2, wherein the compound having a disulfide bond in the molecular chain is cystamine or cystine.

8. A method for culturing cells to produce three-dimensionally organized cells having a three-dimensional cellular structure consisting of cells and cell-produced extracellular matrix, comprising:
   (a) culturing cells on a material comprising a hydrogel produced by crosslinking a water-soluble poly($\gamma$-glutamic acid) at a concentration of 4 to 9% with a crosslinking compound having a disulfide bond in the molecular chain, at an equivalence of functional group in the crosslinking compound of half or more of the equivalence of functional group in the water-soluble poly($\gamma$-glutamic acid), an
   (b) controllably decomposing the hydrogel under a reductive atmosphere or controllably decomposing the hydrogel by contacting it with a reducing agent to separate three-dimensionally organized cells having a three-dimensional cellular structure consisting of cells and cell-produced extracellular matrix.

9. The method according to claim 8, wherein the reducing agent is selected from the group consisting of at least one of glutathione (GSH), dihydrolipoic acid (DHLA) or cysteine (Cys).

10. The method according to claim 8, wherein said crosslinking compound is cystamine, cystine or 3,3'-dithiodipropionic acid.

11. The method according to claim 10, wherein said crosslinking compound is cystamine or cysteine.

* * * * *